(12) United States Patent
Shabanova et al.

(10) Patent No.: US 10,457,465 B2
(45) Date of Patent: Oct. 29, 2019

(54) DISINFECTANT WIPES

(71) Applicant: TRISTEL PLC, Newmarket, Cambridgeshire (GB)

(72) Inventors: Julija Shabanova, Newmarket (GB); Esther Jansen, Newmarket (GB); Matthew Ballinger, Newmarket (GB)

(73) Assignee: TRISTEL PLC, Newmarket (GB)

( * ) Notice: Subject to any disclaimer, the term of this patent is extended or adjusted under 35 U.S.C. 154(b) by 0 days.

(21) Appl. No.: 16/069,314

(22) PCT Filed: Jan. 24, 2017

(86) PCT No.: PCT/EP2017/051437
§ 371 (c)(1),
(2) Date: Jul. 11, 2018

(87) PCT Pub. No.: WO2017/129567
PCT Pub. Date: Aug. 3, 2017

(65) Prior Publication Data
US 2019/0023476 A1  Jan. 24, 2019

(30) Foreign Application Priority Data
Jan. 28, 2016 (GB) .................................. 1601575.2

(51) Int. Cl.
*B65D 81/32* (2006.01)
*A61L 2/18* (2006.01)
(Continued)

(52) U.S. Cl.
CPC ......... *B65D 81/3272* (2013.01); *A01N 59/00* (2013.01); *A61L 2/18* (2013.01);
(Continued)

(58) Field of Classification Search
CPC ............... B65D 83/08; B65D 83/0805; B65D 83/0847; B65D 83/0888; B65D 85/07; B65D 81/22; B65D 81/24
(Continued)

(56) References Cited

U.S. PATENT DOCUMENTS

2005/0258062 A1* 11/2005 Bando .................. A47K 10/421
206/494
2014/0144803 A1* 5/2014 Yamada ............... A47K 10/421
206/494

FOREIGN PATENT DOCUMENTS

EP 0423817 A2 10/1990
EP 1648523 A1 4/2006
(Continued)

*Primary Examiner* — King M Chu
(74) *Attorney, Agent, or Firm* — Hayes Soloway PC

(57) ABSTRACT

A disinfectant wipes system (2) comprising: a flexible sealed container (4) containing a plurality of fabric wipe members (6) and a burstable sachet (12); a first part comprising a first reagent in a carrier medium absorbed or impregnated in the fabric wipe members; and a second part within the burstable sachet (12), the second part miscible with the first part and comprising a second reagent in a carrier medium; wherein the first reagent and the second reagent will react when mixed to provide a disinfectant composition; wherein the container (4) has an opening (14) through which the wipe members (6) and the burstable sachet (12) may pass; the opening (14) releasably sealed by an adhesive-backed label (8); and wherein the burstable sachet (12) is separate from the plurality of wipe members (6) so that it can be removed through the opening (14) without removing any of the plurality of wipe members (6).

9 Claims, 3 Drawing Sheets

(51) Int. Cl.
*A01N 59/00* (2006.01)
*B65D 75/58* (2006.01)
*B65D 83/08* (2006.01)

(52) U.S. Cl.
CPC ..... *B65D 75/5838* (2013.01); *B65D 83/0805* (2013.01); *B65D 2203/02* (2013.01); *B65D 2575/586* (2013.01)

(58) Field of Classification Search
USPC ............................... 206/205, 219, 494, 581
See application file for complete search history.

(56) References Cited

FOREIGN PATENT DOCUMENTS

| | | | |
|---|---|---|---|
| GB | 2503678 | A | 3/2012 |
| JP | 2005255657 | A | 9/2005 |
| WO | 2005011756 | A1 | 2/2005 |
| WO | 2008065551 | A1 | 6/2008 |

\* cited by examiner

DISINFECTANT WIPES

BACKGROUND a. Field of the Invention

The present invention relates to a disinfectant wipes system, notably to apparatus and a method for preparing sporicidal wipes using a two-part chemistry. The invention is particularly for use in disinfecting surfaces, notably surfaces of medical apparatus and equipment, but it is not limited to these uses.

b. Related Art

WO 2005/011756 discloses a two-part sterilant system comprising a first part having a first reagent in a carrier medium and a second part which is miscible with the first part and which comprises a second reagent in a carrier medium. The first reagent and the second reagent react when mixed to provide a sterilising composition. The first part is contained in a pump dispenser whereby it may be dispensed as a fluid, preferably as a foam, and the second part is absorbed or impregnated in at least one fabric member in a sealed container. To prepare a sterilising wipe, a user removes an impregnated wipe from the container, and applies a portion of foam from the sprayer to the wipe. To facilitate mixing of the reagents in the foam and the wipe, the user may fold the wipe in half and crush or rub the folded wipe before opening it out.

The system is particularly useful for preparing wipes in which the disinfecting agent has a limited shelf life, such as chlorine dioxide. However, if many disinfectant wipes are needed in a relatively short space of time, the preparation process can be time consuming.

JP 2005/255657 discloses a single-use device for preparing a sterilizing or deodorant wipe. The device comprises an internal bag which contains an acid and which is laminated to a sheet impregnated with aqueous chlorite solution. The internal bag and sheet are contained in an external bag which is sealed by thermally fusing opposed end parts. The external bag is pressed or subjected to impact to break the internal bag and allow the acid to flow into the laminated sheet. This action results in the sheet being impregnated with chlorine dioxide. The user then removes the entire contents of the external bag (disinfectant sheet laminated to the internal bag), which will require bursting or tearing open of the external bag.

SUMMARY OF THE INVENTION

Aspects of the invention are specified in the independent claims. Preferred features are specified in the dependent claims.

The invention allows the preparation of batches of disinfectant wipes in a sealed container. The disinfecting agent is preferably chlorine dioxide, which has excellent bactericidal and sporicidal properties. A batch of chlorine dioxide-impregnated disinfectant wipes according to an aspect of the invention can be quickly prepared and has a shelf-life of up to eight hours.

The entire disinfectant wipes system is contained and activated within a single pack, which provides a convenient and easy way to prepare a batch of disinfectant wipes.

BRIEF DESCRIPTION OF THE DRAWINGS

The invention will now be further described, by way of example only, with reference to the following drawings, in which.

DETAILED DESCRIPTION

Figure 1:
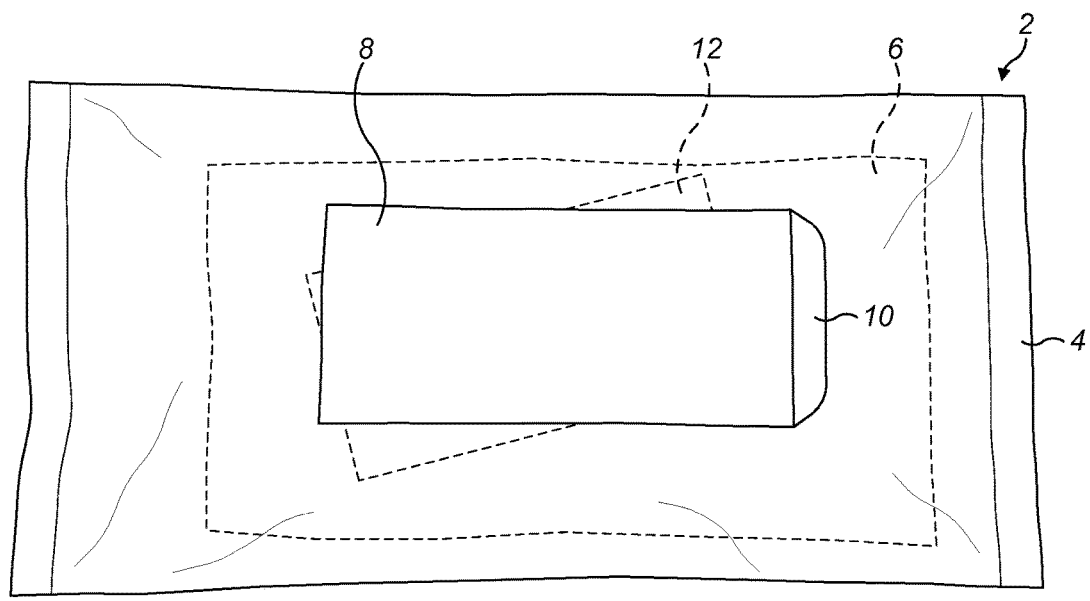
FIGS. 1 and 2 are top plan views of a disinfectant wipes system in accordance with an embodiment of the present invention.

The disinfectant wipes system 2 shown in FIG. 1 comprises a flexible sealed container 4 containing a plurality of fabric wipe members 6 and a burstable sachet 12. The fabric wipe members 6 are impregnated with a first part comprising a first reagent in a carrier medium. In this example, there are 20 wipe members which are interleaved. The first part is, in this embodiment, 210 ml of an aqueous solution of citric acid (5-20 g/kg).

The burstable sachet 12 contains a second part which is miscible with the first part and which comprises a second reagent in a carrier medium. In this example, the second part comprises 70 ml of an aqueous solution of sodium chlorite (0.5-5 g/kg).

The first reagent and the second reagent react when mixed, to provide a disinfectant composition. In this example the disinfectant composition is aqueous chlorine dioxide (0.1-1 g/kg $ClO_2$) produced by the reaction between sodium chlorite and citric acid.

Figure 2:
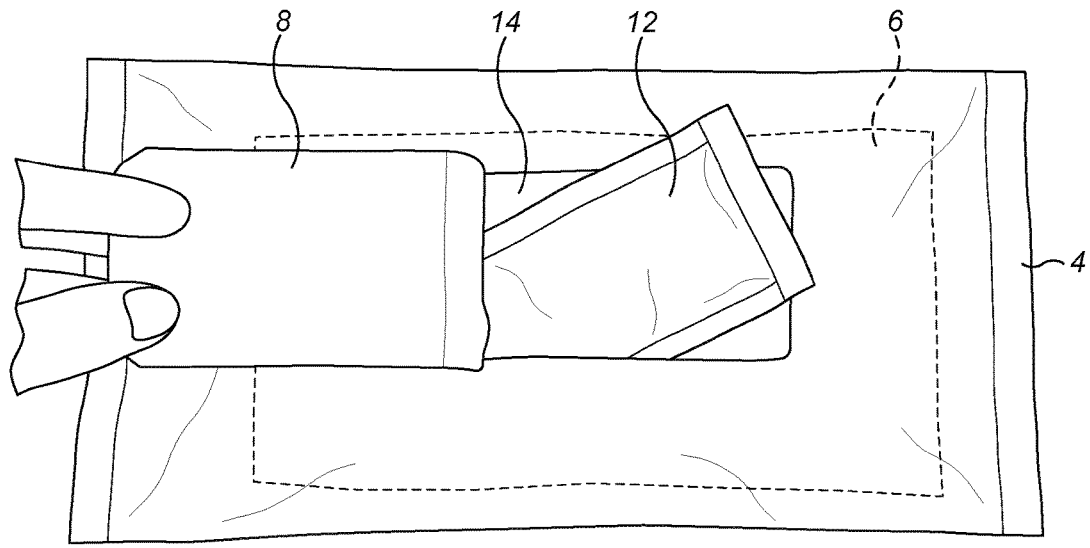

The exemplified container 4 is a pack formed from a plastics material and has an opening 14 (FIG. 2) through which the wipes 6 and burstable sachet 12 may be removed from the container 4. In normal use, the opening 14 is covered by an adhesive-backed label 8 which seals the inside of the container 4 from the external environment. The adhesive label 8 is removable and resealable; it includes a non-adhesive tab portion 10 to aid peeling back of the label.

Figure 3:
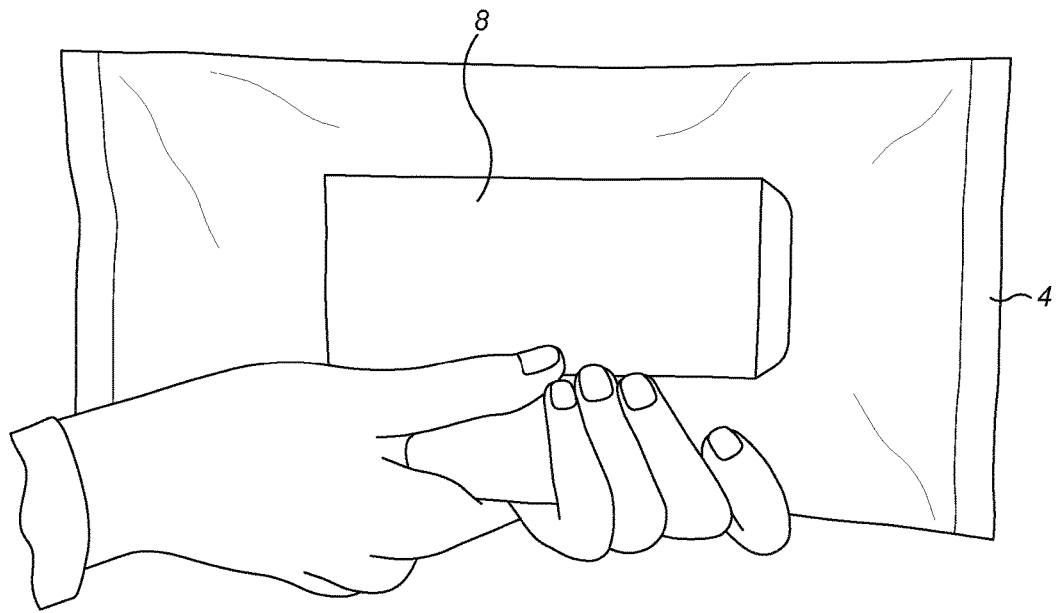
FIGS. 3 and 4 show a stages in preparation of the disinfectant wipes.
Figure 5:
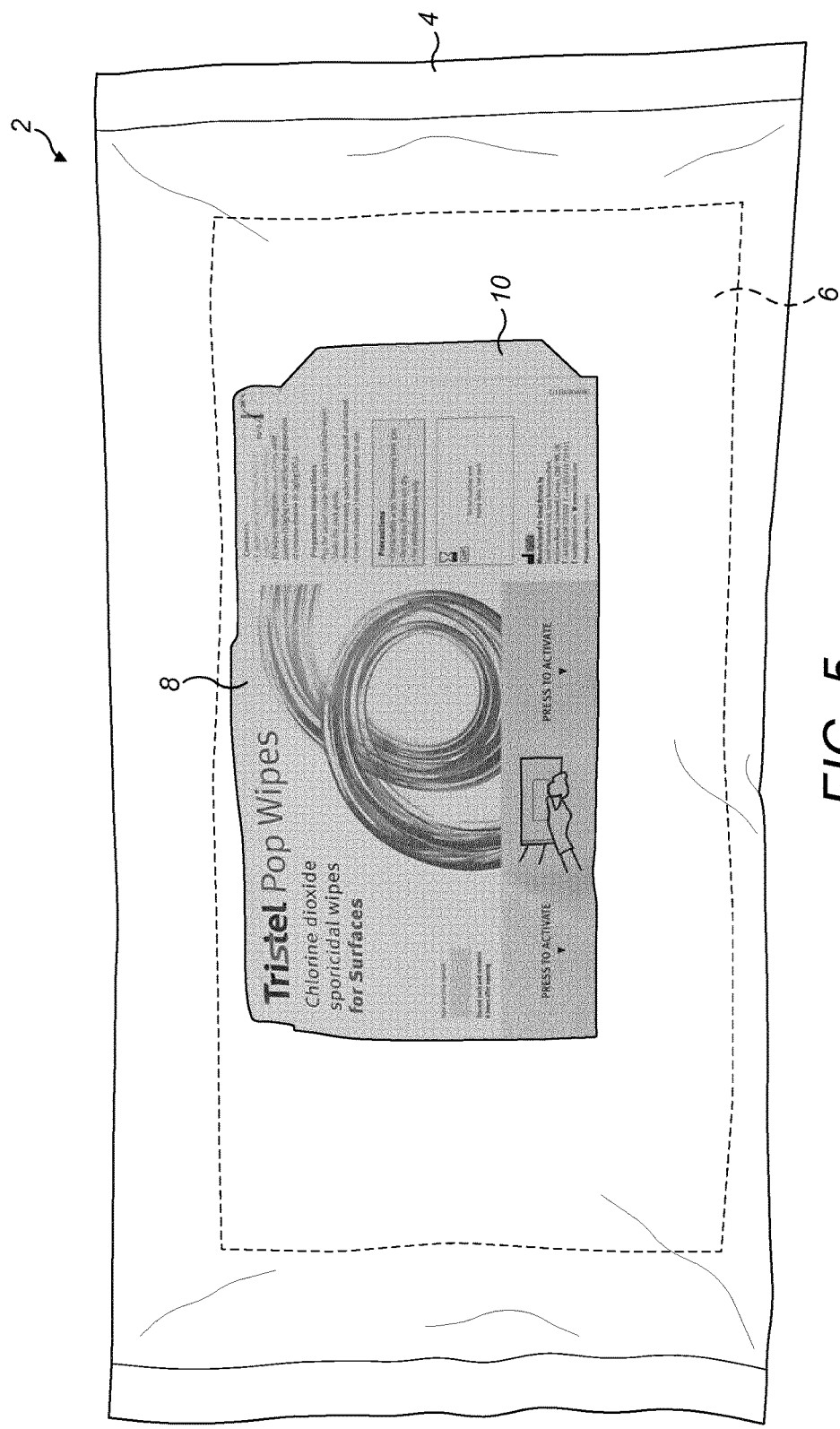
FIG. 5 illustrates an activated disinfectant wipes system in accordance with another embodiment of the invention.

To prepare a batch of disinfectant wipes, the user presses the container 4 (FIG. 3) so as to burst the sachet 12 and release the second part (sodium chlorite solution) within the sealed container 4. To disperse the second part solution evenly between the wipes 6, the user gently shakes the container 4. Instructions for use may conveniently be provided on the label 8 (FIG. 5).

Figure 4:
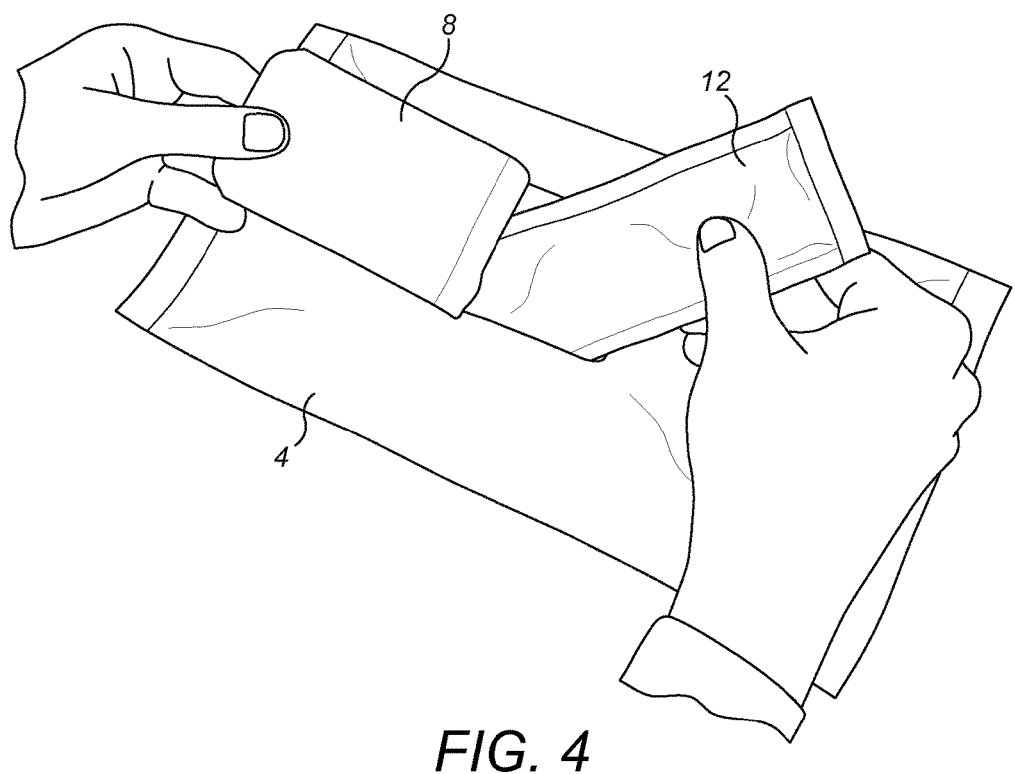

The user peels back the label 8 and removes the empty sachet 12 from the container 4 (FIG. 4). The user then reseals the container 4. After 10 minutes from when the sachet 12 is burst and the contents distributed, the disinfectant wipes 6 are ready for use. To dispense an activated disinfectant wipe, a user peels back the label 8 and pulls a wipe out through the opening 14 before replacing the label over the opening.

The activated disinfectant wipes are sporicidal within one to two minutes' contact time with a surface. Disinfectant wipes in the container remain usable for at least eight hours after activation.

EXPERIMENTAL

The activity of disinfectant wipes according to the present invention (code name DVNT021 Burst) was assessed by the Hospital Infection Research Laboratory, Birmingham UK (part of University Hospital Birmingham NHS Foundation Trust), using a test disinfectant containing 0.2 g/kg $ClO_2$.

Summary of Test Method

The modified method for ready-to-use products was employed. This method allows ready-to-use products to be tested at an effective concentration of 97% (method described in EN 13727 (2013)). Suspensions of *C. difficile* and *B. subtilis* spores were prepared, each containing at least $10^8$ viable spores/ml. The test method involves mixing 0.1 ml of the test spore suspension with 0.2 ml of soil (1.5% w/v albumin) and then adding 9.7 ml of test disinfectant. After the required contact time, 0.1 ml is removed to 9.9 ml of recovery broth (8.9 ml neutralizer and 1 ml water). Surviving *B. subtilis* spores were detected by plating onto Tryptone Soya Agar, and incubating for 18-24 hours at 37° C. The plates were incubated for a further 24 hours at 37° C., to check for additional growth. Surviving *C. difficile* spores were detected by plating onto Columbia Agar with 5% sheep blood, and incubating under anaerobic conditions at 37° C. for 3-5 days.

Requirement

The test requirements for EN 13704 (Phase 2 Step 1 sporicidal test) is for a $log_{10}$ reduction in 60 minutes.

Results

Efficacy of DVNT021 Burst Against *Bacillus subtilis* Spores

All Tests Carried Out in Duplicate

TABLE 1

| | | | $Log_{10}$ Reduction Achieved | | | | | |
| | | | Clean Conditions (0.03% Albumin) '0 hours' | | | Clean Conditions (0.03% Albumin) '8 hours' | | |
| | $Log_{10}$ Initial Count | | | | | | | |
| Test organism | (challenge) | Time | Test 1 | Test 2 | Mean | Test 1 | Test 2 | Mean |
| Bacillus subtilis (NCTC 10400) | 7.61 | 1 min | 1.79 | 1.71 | 1.75 | 1.84 | 2.23 | 2.04 |
| | | 2 min | 3.51 | 3.39 | 3.45 | 3.92 | 3.94 | 3.93 |

Efficacy of DVNT021 Burst against *Clostridium difficile* spores

All Tests Carried Out in Duplicate

TABLE 2

| | | | $Log_{10}$ Reduction Achieved | | | | | |
| | | | Clean Conditions (0.03% Albumin) '0 hours' | | | Clean Conditions (0.03% Albumin) '8 hours' | | |
| | $Log_{10}$ Initial Count | | | | | | | |
| Test organism | (challenge) | Time | Test 1 | Test 2 | Mean | Test 1 | Test 2 | Mean |
| Clostridium difficile (NCTC 11209) | 7.06 | 1 min | 4.58 | >5.06 | >4.82 | >5.06 | 4.58 | >4.82 |
| | | 2 min | >5.06 | >5.06 | >5.06 | >5.06 | 4.46 | >4.76 |

Comparative Example

As a comparison. sodium dichloroisocyanurate (NaDCC)*. at a concentration producing 500 ppm freely available chlorine, gave the following results:

*The product used was a commercially-available formulation. These results are included as an internal control for the spore suspension.

TABLE 3

| | $Log_{10}$ Initial Count | Contact | $Log_{10}$ Reduction Achieved Clean Conditions (0.03% Albumin) | | |
| Test organism | (challenge) | time | Test 1 | Test 2 | Mean |
| Clostridium difficile (NCTC 11209) | 7.10 | 1 min | 0.41 | 0.02 | 0.22 |
| | | 5 min | 1.06 | 1.15 | 1.11 |
| | | 60 min | 6.10 | 5.50 | 5.80 |

TABLE 4

| | $Log_{10}$ Initial Count | Contact | $Log_{10}$ Reduction Achieved Clean Conditions (0.03% Albumin) | | |
| Test organism | (challenge) | time | Test 1 | Test 2 | Mean |
| Bacillus subtilis (NCTC 10400) | 7.44 | 1 min | 0.24 | 0.60 | 0.42 |
| | | 5 min | 0.44 | 0.38 | 0.41 |
| | | 60 min | 2.84 | 2.49 | 2.67 |

CONCLUSION

Tests carried out with DVNT021 Burst demonstrated a >3 log 10 reduction in spores of *Bacillus subtilis* at 20° C. under clean (0.03% w/v albumin) conditions within 2 minutes, for both the '0 hour' and '8 hour' solutions. Against spores of *Clostridium difficile*, DVNT021 Burst achieved a >4 $log_{10}$ reduction under clean conditions within 1 minute, for both the '0 hour' and '8 hour' solutions.

EN 13704 has a requirement for a ≥3 $log_{10}$ reduction in 60 minutes. Therefore, DVNT021 Burst fulfils the test criteria under clean conditions against *Bacillus subtilis* within 2 minutes, and *Clostridium difficile* within 1 minute, both with a fresh solution ('0 hour') and one aged for 8 hours ('8 hour').

The fabric wipe members may be formed from any suitable fabric, either woven or non-woven. They may be of natural or man-made fibres, for example polyester, cotton, cellulose or mixtures thereof. Other suitable fabrics will be well known to those skilled in the textile or fabric arts.

Aqueous chlorine dioxide has a characteristic yellow colour. When a user observes that the contents of the container 4 are yellow after bursting of the sachet, this provides confirmation of mixing. To augment the natural colour, the second part may optionally include a coloured component so that a visual indication of the coverage of the wipes with the second part can be made.

Although the invention is exemplified with reference to a first part containing aqueous citric acid and a second part containing aqueous sodium chlorite, it will be appreciated that the invention is not limited to this embodiment. For example, the first part could contain sodium chlorite and the second part could contain citric acid. Other reagents, which will be well known per se to those skilled in the art may alternatively be employed, either for producing chlorine dioxide as the disinfectant or for producing an alternative disinfectant such as peracetic acid.

The invention claimed is:

1. A disinfectant wipes system comprising:
   a flexible sealed container containing a plurality of fabric wipe members and a burstable sachet;
   a first part comprising a first reagent in a carrier medium absorbed or impregnated in the fabric wipe members; and
   a second part within the burstable sachet, the second part miscible with the first part and comprising a second reagent in a carrier medium;
      wherein the first reagent and the second reagent will react when mixed to provide a disinfectant composition;
      wherein the container has an opening through which the wipe members and the burstable sachet may pass; the opening releasably sealed by an adhesive-backed label; and
      wherein the burstable sachet is separate from the plurality of wipe members so that it can be removed through the opening without removing any of the plurality of wipe members.

2. A disinfectant wipes system according to claim 1, wherein the label includes a non-adhesive tab portion.

3. A disinfectant wipes system according to claim 1, wherein the first reagent and the second reagent react when mixed to produce chlorine dioxide.

4. A disinfectant wipes system according to claim 1, wherein the first reagent is an acid and the second reagent is a chlorite.

5. A disinfectant wipes system according to claim 1, wherein at least one of the first part and the second part includes an indicator reagent that changes colour when the parts are mixed together.

6. A method of preparing a plurality of disinfectant wipes, the method comprising taking a disinfectant wipes system as specified in claim 1, and pressing the sealed container to burst the sachet.

7. A method according to claim 6, further comprising unsealing the container and removing the burst sachet from the container.

8. A method according to claim 7, further comprising resealing the container after removal of the burst sachet.

9. A method according to claim 6, further comprising waiting at least two minutes from the time when the sachet is burst before dispensing a disinfectant wipe from the container.

* * * * *